United States Patent
Ying et al.

(10) Patent No.: US 8,501,741 B2
(45) Date of Patent: Aug. 6, 2013

(54) OPTICALLY ACTIVE COMPOUND OF PRULIFLOXACIN FOR TREATING INFECTION AND PREPARATION METHOD THEREOF

(75) Inventors: Jun Ying, Guangdong (CN); Feng Peng, Guangdong (CN); Yuping Wang, Guangdong (CN); Suiwei An, Guangdong (CN); Jinqiang Liang, Guangdong (CN); Beimei Liang, Guangdong (CN); Qingchun Ni, Guangdong (CN); Cheng Luo, Guangdong (CN)

(73) Assignee: Hainan Hualon Pharmaceutical Co., Ltd., Hainan (CN)

( * ) Notice: Subject to any disclaimer, the term of this patent is extended or adjusted under 35 U.S.C. 154(b) by 0 days.

(21) Appl. No.: 13/522,290

(22) PCT Filed: Oct. 22, 2010

(86) PCT No.: PCT/CN2010/078020
§ 371 (c)(1),
(2), (4) Date: Jul. 13, 2002

(87) PCT Pub. No.: WO2011/085606
PCT Pub. Date: Jul. 21, 2011

(65) Prior Publication Data
US 2012/0302580 A1    Nov. 29, 2012

(30) Foreign Application Priority Data
Jan. 13, 2010  (CN) .......................... 2010 1 0019328

(51) Int. Cl.
*A61K 31/496*  (2006.01)
*C07D 495/04*  (2006.01)

(52) U.S. Cl.
USPC ..................................... 514/253.03; 544/361

(58) Field of Classification Search
USPC ..................................... 514/253.03; 544/361
See application file for complete search history.

(56) References Cited

U.S. PATENT DOCUMENTS 5,086,049 A * 2/1992 Kise et al. ................ 514/210.16

OTHER PUBLICATIONS

Segawa et al., Studies on Pyridonecarboxylic Acids. IV. Synthesis and Antibacterial Activity Evaluation of S-(−)- and R-(+)-6-Fluoro-1-methyl-4-oxo-7-(1-piperazinyl)-4H-[1,3]thiazeto[3,2-a]quinoline-3-carboxylic Acids, 1995, Chem. Pharm. Bull., 43(7), 1238-1240.*

* cited by examiner

*Primary Examiner* — Kristin Vajda
(74) *Attorney, Agent, or Firm* — Christie, Parker, Hale, LLP

(57) ABSTRACT

Anti-infection levorotatory optically active compound (S-configuration) of prulifloxacin represented by the following formula (1) and preparation method thereof are disclosed. Said method utilizes levorotatory ulifloxacin as the raw material and the reaction is conducted in organic solvent in the presence of alkaline materials, wherein the reaction temperature is −20° C.~60° C. and the reaction time is 15 minutes to 24 hours.

(I)

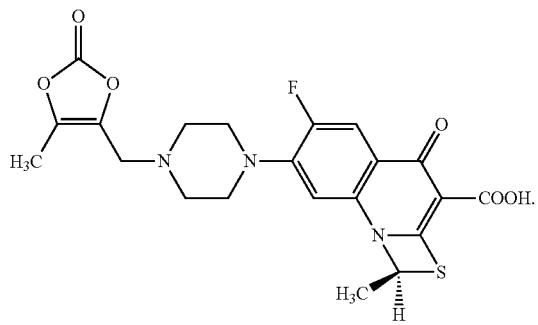

9 Claims, 2 Drawing Sheets

OPTICALLY ACTIVE COMPOUND OF PRULIFLOXACIN FOR TREATING INFECTION AND PREPARATION METHOD THEREOF

CROSS-REFERENCE TO RELATED APPLICATION(S)

This application is a National Phase Patent Application and claims priority to and benefit of International Application Number PCT/CN2010/078020, filed on Oct. 22, 2010, which claims priority to and benefit of Chinese Patent Application Number 201010019328.X, filed on Jan. 13, 2010, the entire disclosure of which are incorporated herein by reference.

TECHNICAL FIELD

The present invention relates to an optically active thiazetoquinoline carboxylic acid antimicrobial and preparation method thereof and specifically relates to optically active compound of prulifloxacin and its oral preparation and preparation method thereof.

BACKGROUND TECHNOLOGIES

Quinolone is a kind of anti-infective drugs synthesized in recent years and clinically used for treating respiratory, gastrointestinal, urinary, dermatological, gynecological, surgical diseases and etc. extensively, with very good results. Prulifloxacin, the chemical name of which is (±)6-fluoro-1-methyl-7-[4-(5-methyl-2-oxo-1,3-dioxolen-4-yl)methyl-1-piperazinyl]-4-oxo-4H-[1,3]thiazeto[3,2-α]quinoline-3-carboxylic acid, is a quinolone drug developed together by Nippon Shinyaku Co. Ltd. and Meiji Seika Kaisha Ltd. Prulifloxacin is the third generation broad spectrum antibacterial drug of the fluoroquinolone class with broad spectrum antibacterial effects on both gram-positive bacteria and gram-negative bacteria and thereby can be used for treating systemic infection. In particular, antibacterial effects of prulifloxacin on *Pseudomonas aeruginosa* go beyond that of other commercially available antibacterial drugs of the fluoroquinolone class significantly. Results of clinical trials show that prulifloxacin have better therapeutic effects on dermatological infections, surgical infections, respiratory organ infections, urinary tract infections, biliary tract infections, infective enteritis, gynecological infections, ophthalmological infections, and otolaryngological infections.

Besides the common features of fluoroquinolone drugs, prulifloxacin have the following characteristics in comparison with other drugs of the same class: 1. its antibacterial effects on gram-positive bacteria are close to gatifloxacin but its effects on gram-negative bacteria such as *Pseudomonas aeruginosa* and etc. exceed similar products, for example, ciprofloxacin, ofloxacin, levofloxacin and gatifloxacin, and it also has effects on *Pseudomonas aeruginosa* of drug resistance. 2. It can be absorbed well via oral administration without accumulation in the body or distribution in cerebrospinal fluid and therefore has little side effect. 3. Its half-life is as long as 8-9 hours so that the times of taking medicines are less. 4. It takes effects fast and its peak blood concentration is attained within 0.5-1 hours. It has strong antibacterial activity. 5. It has hardly phototoxicity or neurotoxicity, so it is the safest product among fluoroquinolones at present.

Studies show that ulifloxacin has very strong antibacterial activity both in vivo and in vitro and has almost the same antibacterial spectrum as prulifloxacin: broad spectrum antibacterial effects on both gram-positive bacteria and gram-negative bacteria, strong antibacterial activity on *Pseudomonas aeruginosa* and other gram-negative bacteria particularly. Ulifloxacin has one carbon atom chiral center (1-C) resulting in two enantiomers of ulifloxacin. As reported in a publication (Chem. Pharm. Bull., 43(7), 1238-40 (English) 1995), the Japanese originator pharmaceutical company conducted pharmacodynamics studies on small samples obtained through chiral preparation chromatographic column and found that the antibacterial activity of levo-enantiomer is 2 to 8 times stronger than that of dextro-enantiomer.

After prulifloxacin is absorbed via oral administration, the side chain in 4' site of piperazinyl is removed in the presence of hepatic enzyme, which results in that prulifloxacin is converted to ulifloxacin with the antibacterial activity and thereby taking action. The chiral center 1-C is not the metabolic site in this intracorporal process, so the metabolite of levo-prulifloxacin in the presence of hepatic enzyme is levo-ulifloxacin which has antibacterial effects. Predictably, the prospect for application of levo-prulifloxacin would be great. Although, there is one carbon atom chiral center (1-C) in the prulifloxacin structure, only racemic form (optical rotation $[\alpha]^{20}_D \approx 0°$) can be obtained according to the prior arts. Thus, it is necessary to develop optically active prulifloxacin.

SUMMARY OF THE INVENTION

The objective of the present invention is to provide an optically active stereoisomer of prulifloxacin and preparation method thereof as well as its composition.

To achieve the above-mentioned objective, the inventor conducted studies on stereo configuration of current prulifloxacin and provided an optically active compound of prulifloxacin for anti-infection, which is a quinolone compound as shown in the following general formula 1, and the physiologically acceptable pharmaceutical salts thereof, wherein the chemical name of formula 1 is S-(−)-6-fluoro-1-methyl-7-[4-(5-methyl-2-oxo-1,3-dioxolen-4-yl)methyl-1-piperazinyl]-4-oxo-4H-[1,3]thiazeto[3,2-α]quinoline-3-carboxylic acid (levo-prulifloxacin for short); its stereo configuration is S configuration; it has optical property of levorotatory polarized light:

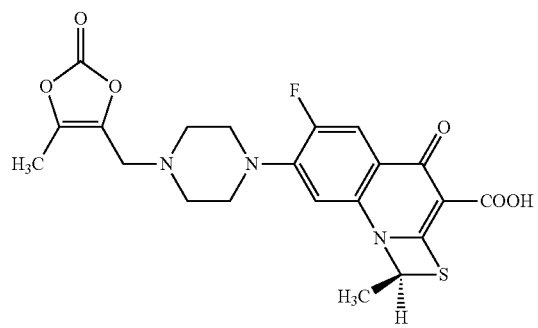 [SMILES: Cc1oc(=O)oc1CN1CCN(c2cc3c(cc2F)c(=O)c(C(=O)O)c2n3[C@H](C)S2)CC1]

The physiologically acceptable pharmaceutical salts of the compound described herein may be the salts formed with any one organic acid selected from the group of acetic acid, glycine, methanesulfonic acid, lactic acid, glutamic acid, mandelic acid, gluconic acid, aspartic acid, citric acid, succinic acid, fumaric acid, maleic acid, oxalic acid, lactobionic acid and benzene sulfonic acid, may also be the salts formed with any one inorganic acid selected from the group of hydrochloric acid, hydrobromic acid, sulfuric acid and phosphoric acid.

For aspartic acid and glutamic acid, the DL, D and L configurations may be selected respectively. The salts formed with any one organic acid selected from methanesulfonic acid, lactic acid, glutamic acid, gluconic acid and aspartic acid are preferred.

The compound of the present invention may be prepared according to the following method:

S-(−) ulifloxacin (as shown in formula 2 below) as raw material and the compound as shown in the following formula 3 are reacted in organic solvent in the presence of alkaline material. The reaction formula is shown below:

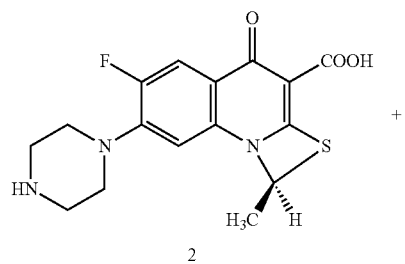

2

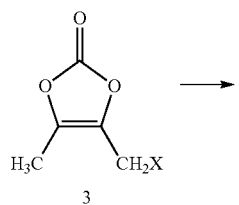

3

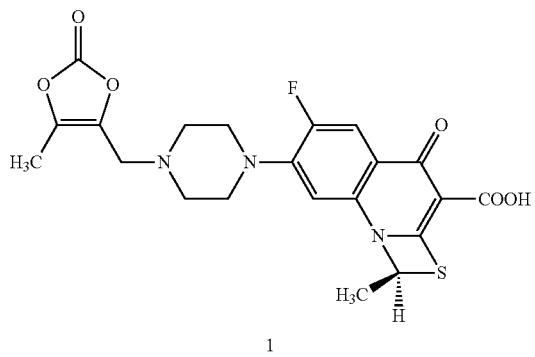

1

Wherein X in formula 3 is a halogen or p-methylsulfonyloxy, preferably bromine-containing compound, the chemical name of which is 4-bromomethyl-5-methyl-1,3-dioxolen-2-one.

Reaction temperature is usually −20~60° C., preferably −10~30° C.

Reaction time varies depending on the type and the amount of solvents and alkaline materials and reaction temperature, usually 15 minutes to 24 hours.

Raw material ratio: the ratio of levo-ulifloxacin to the compound of formula 3 to alkaline material is 1:0.8~2:0.5~5 by gram molecule.

The solvent is organic solvent, preferably N,N-dimethylformamide or N,N-dimethylacetylamide or dimethyl sulfoxide or other inactive solvents.

Said alkaline material is inorganic base or organic base, wherein inorganic base may be potassium carbonate, potassium bicarbonate, sodium carbonate, sodium bicarbonate, calcium carbonate or calcium bicarbonate and the like; organic base may be triethylamine, diisopropylamine, N,N-Diisopropylethylamine, tributylamine, N-methylmorpholine, N,N-dimethylaniline or imidazole and the like. Potassium carbonate, potassium bicarbonate, triethylamine, diisopropylamine, or N,N-diisopropylethylamine is preferred.

S-(−)-ulifloxacin and R-(+)-ulifloxacin are prepared according to the method disclosed in CN101550142A.

Japanese scholars Masato Matsuoka et al. have proved the absolute configuration of optically pure prulifloxacin. The study (see the publication Chem. Pharm. Bull. 43(7) 1238-1240 (1995)) verifies that (−)-ulifloxacin is S configuration while (+)-ulifloxacin is the enantiomer of R configuration by applying chemical methods together with single-crystal X-ray diffraction.

In the chemical reaction process of preparing optically active prulifloxacin from the above-mentioned optically active ulifloxacin, the chiral center 1-C is not involved in the chemical reaction and under mild reaction conditions the configuration of the chiral center 1-C remains the same, which can be proved by the following experiment results: the products retain the same property of polarized light as the raw material (that is levorotatory ulifloxacin produces levorotatory prulifloxacin while dextrorotatory ulifloxacin produces dextrorotatory prulifloxacin); the chiral high performance liquid chromatography suggests that the ratios of two optical isomers before or after reaction remain unchanged, which proves configuration of the chiral center 1-C is maintained the same. Thus, the prulifloxacin prepared from the raw material S-ulifloxacin still keeps the same S configuration and the final product is S-prulifloxacin.

Accordingly, R-prulifloxacin can be prepared from R-(+)-ulifloxacin and the compound of formula 3 by the method described hereinbefore.

The reaction formula is depicted below:

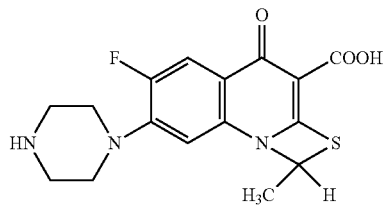

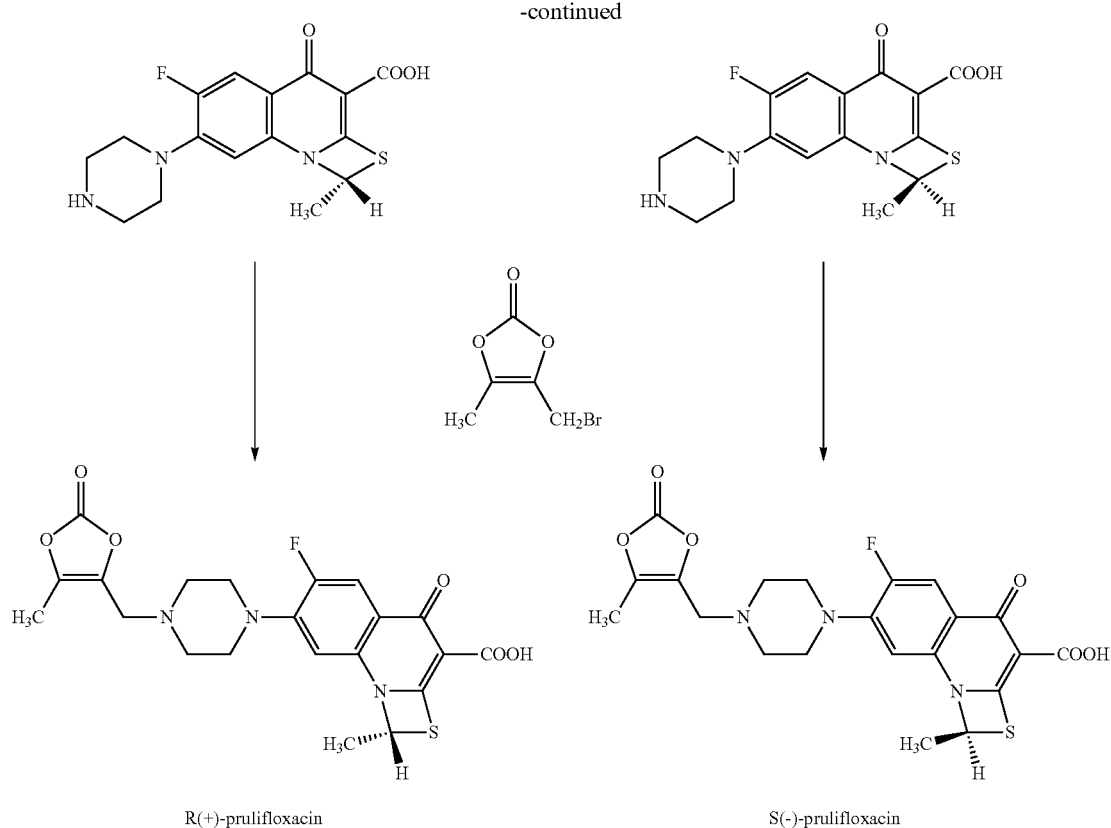

R(+)-prulifloxacin    S(−)-prulifloxacin

S-prulifloxacin prepared in accordance with the present invention is determined to be laevorotatory by optical rotation measurement, so it is S-(−)-prulifloxacin. R-prulifloxacin prepared in accordance with the present invention is determined to be dextrorotatory by optical rotation measurement, so it is R-(+)-prulifloxacin.

The present invention studied the absorption features of S-(−)-prulifloxacin and R-(+)-prulifloxacin on circular polarized light by circular dichroism spectroscopy. The two spectrograms are mirror images of each other, which proves that S-(−)-prulifloxacin and R-(+)-prulifloxacin are enantiomer of each other.

Comparing the circular dichroism spectrogram as depicted in FIG. 4 with the circular dichroism spectrogram of analogue of the similar structure with known absolute configuration as disclosed in the publication Chem. Pharm. Bull. 47(12) 1765-1773 (1999), it is found that (−)-prulifloxacin has similar Cotton effect to the two analogues reported in the publication, ethyl S-(−)-6,7-difluoro-1-methyl-4-oxo-4H-[1,3]thiazeto[3,2-α]quinoline-3-carboxylate and ethyl S-(−)-6,7-difluoro-1-fluoromethyl-4-oxo-4H-[1,3]thiazeto[3,2-α]quinoline-3-carboxylate; so does (+)-prulifloxacin. The results also verify on the other hand that the absolute configuration of levo-prulifloxacin of the present invention is S type while the absolute configuration of dextro-prulifloxacin is R type.

The compound of the present invention and physiologically acceptable acid can be prepared to salts: dissolving or suspending S-(−)-prulifloxacin in solvent such as chloroform, DMF and the like; adding into acid or acid solution (for example, hydrochloric acid or hydrogen chloride-methanol solution and the like) while stirring; precipitating and filtering to obtain solid salt from the solvent solution, or alternatively removing solvent from the salt solution directly by concentration, spray drying and the like to obtain the salt of S-(−)-prulifloxacin. The obtained solid may be further recrystallized.

Common organic acid may be any one organic acid selected from the group of acetic acid, glycine, methanesulfonic acid, lactic acid, glutamic acid, mandelic acid, gluconic acid, aspartic acid, citric acid, succinic acid, fumaric acid, maleic acid, oxalic acid, lactobionic acid and benzene sulfonic acid; inorganic acid may be any one inorganic acid selected from the group of hydrochloric acid, hydrobromic acid, sulfuric acid and phosphoric acid. For aspartic acid and glutamic acid, the DL, D and L configurations may be selected respectively. It is preferred to select methanesulfonic acid, lactic acid, glutamic acid, gluconic acid or aspartic acid.

S-(−)-prulifloxacin of the present invention or pharmaceutical salts thereof may be used as effective component, and prepared to oral preparation by adding pharmaceutical adjuvants.

S-(−)-prulifloxacin of the present invention or its salts may be administered orally and the appropriate dosage is 0.1~100 mg/kg body weight/day base on levo-prulifloxacin, most preferably 2~3 mg/kg body weight/day. Therefore, said compound or pharmaceutical salts thereof as effective components are mixed with pharmaceutical adjuvants, such as excipient, disintegrant, binder, lubricant, antioxidant, coating agent, colorant, aromatic, surfactant and the like to prepare tablet, dispersible tablet, capsule, syrup, solvent, granule, emulsion, suspension, dry suspension and other oral preparations, wherein tablet may be either ordinary tablet or coated tablet. The content of said compound in said preparation is 0.1%~100% (weight ratio).

Advantages of the present invention lie in that:

The compound of the present invention levo-prulifloxacin and physiologically acceptable salts thereof have stronger anti-bacterial activity but low toxicity and can thereby substitute for the existing anti-bacterial drug prulifloxacin and physiologically acceptable salts.

Figure 1:
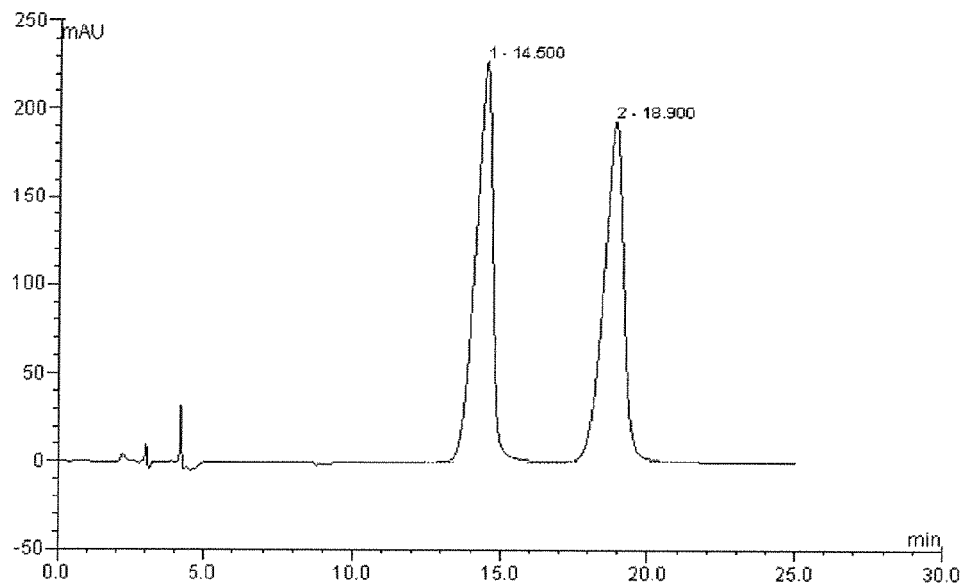
FIG. 1 depicts chiral HPLC chromatogram of racemic prulifloxacin.
Figure 2:
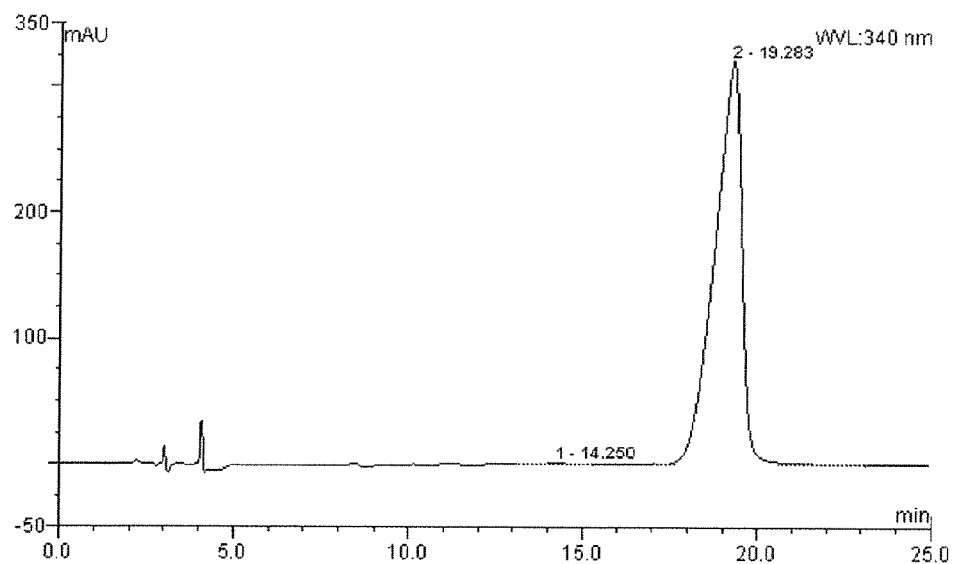
FIG. 2 depicts chiral HPLC chromatogram of dextro-prulifloxacin.
Figure 3:
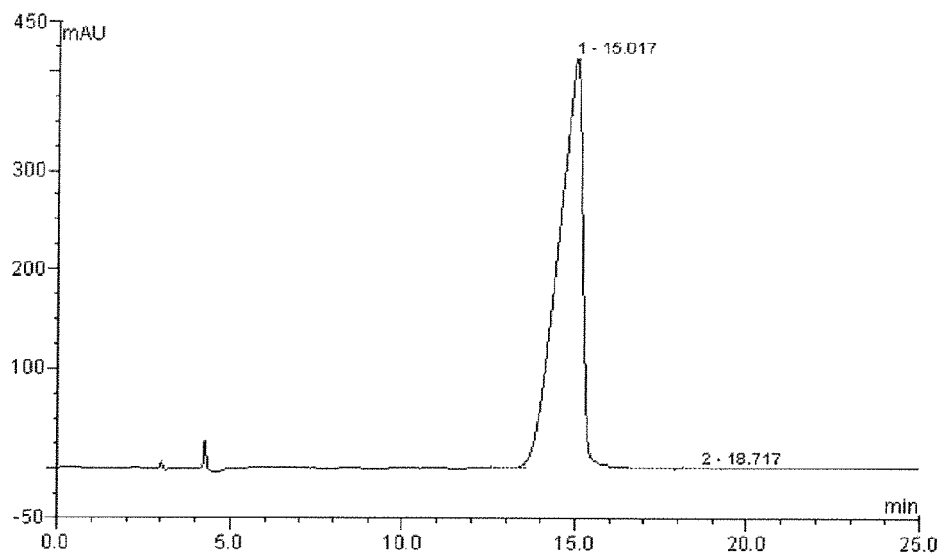
FIG. 3 depicts chiral HPLC chromatogram of levo-prulifloxacin.

The technical scheme of the present invention is further illustrated hereinafter by combining embodiments and figures, but not limited to the following examples.

DESCRIPTION OF PREFERRED EMBODIMENTS

Example 1

Preparation of (S)-(−)-Uliflourxacin 105 g of racemic uliflourxacin was dissolved in 1,500 mL of dimethyl sulfoxide. 27 g of D-tartaric acid was dissolved in 405 mL of dimethyl sulfoxide dropwise while stirring. After stirring at room temperature for 20 hours, the precipitate was filtered. The collected solid was dried under vacuum to obtain 86 g solid, which was recrystallized in dimethyl sulfoxide to obtain 37 g of levouliflouxacin-D-tartrate, with C49.08%, H5.06%, N9.50%, S7.44% shown by elemental analysis (molecular formula: $C_{16}H_{16}FN_3O_3S.1/2C_4H_6O_6.H_2O$, calculated values: C48.86%, H4.78, N9.50%, S7.25%). Said salt was added into water to obtain a suspension, and the pH value was adjusted to 7-8 with 2% NaOH aqueous solution while stirring. After precipitation, filtration, and drying, 24.5 g of (S)-uliflourxacin was obtained, having a chemical name (S)-(−)-6-fluoro-1-methyl-4-oxo-(1-piperazinyl)-1H,4H-[1,3]thiazeto[3,2-α]quinoline-3-carboxylic acid.

Specific rotation $[\alpha]^{20}_D=-133°$ (c=0.5, 0.1 mol/L methanesulfonic acid); $^1$H-NMR (DMSO-$d_6$) δ2.11 (3H, d, j=6.2 Hz), 2.87 (4H, m), 3.19 (4H, m), 6.40 (1H, q, j=6.2 Hz), 6.89 (1H, d, j=7.4 Hz), 7.79 (1H, d, j=13.9 Hz), optical purity e.e. 96%.

Example 2

Preparation of (R)-(+)-Uliflourxacin 105 g of racemic uliflourxacin was dissolved in 1,500 mL of DMSO. 27 g of L-tartaric acid was dissolved in 405 mL dimethyl sulfoxide dropwise while stirring to allow that the solution became turbid and the precipitation occurred. The solution was stirred at room temperature for 20 hours and then filtered. The collected solid was dried under vacuum to obtain 82 g solid which was recrystallized in dimethyl sulfoxide to obtain 34 g of dextrouliflourxacin-L-tartarte. Said salt was added into water to obtain a suspension, and the pH value was adjusted to 7-8 with 2% NaOH aqueous solution while stirring. After filtration and drying, 22 g of (R)-uliflourxacin was obtained, having a chemical name (R)-(+)-6-fluoro-1-methyl-4-oxo-(1-piperazinyl)-1H,4H-[1,3]thiazeto[3,2-a]quinoline-3-carboxylic acid.

Specific rotation $[\alpha]^{20}_D=+132.4°$ (c=0.5, 0.1 mol/L methanesulfonic acid), optical purity e.e. 96%.

Example 3

Preparation of S-(−)-Prulifloxacin 3.49 g (0.01 mol) of S-(−)-uliflourxacin prepared in Example 1, 2.02 g (0.02 mol) of triethylamine and 20 ml of dimethylformamide (hereinafter referred to as DMF) were mixed and stirred. After the solution was cooled to −5~5° C., 0.012 mol of 4-bromomethyl-5-methyl-1,3-dioxolen-2-one (hereinafter referred to as DMDO-Br) in DMF (5 ml) solution was added thereinto, followed by stirring at −5~5° C. for 3 hours. The reaction solution was poured into 100 ml of ice water, stirred for 30 minutes, and then filtered. The filter residue was washed with water. The solid was collected and dried under vacuum. After recrystallization from acetonitrile, 2.9 g of S-(−)-prulifloxacin was obtained, having a chemical name: S-(−)-6-fluoro-1-methyl-7-[4-(5-methyl-2-oxo-1,3-dioxolen-4-yl)methyl-1-piperazinyl]-4-oxo-4H-[1,3]thiazeto[3,2-α]quinoline-3-carboxylic acid, with a purity of 98% and a yield rate of 63%. Specific rotation $[\alpha]^{20}_D=-108°$ (c=0.5, 0.1 mol/L methanesulfonic acid)

Example 4

Preparation of R-(+)-Prulifloxacin

R-(+)-prulifloxacin prepared in Example 2 was used as raw material to prepare 2.7 g of target product R-(+)-prulifloxacin in accordance with the method as described in Example 3, with a yield rate of 60.7% and a purity of 98%. Specific rotation $[\alpha]^{20}_D=+108°$ (c=0.5, 0.1 mol/L methanesulfonic acid).

Experimental Example 1

Determination of Structure of Prulifloxacin

The following routine structure identification assays were conducted on the sample prepared in Example 3.

Results of Element Analsis ($C_{21}H_{20}FN_3O_6S$):

TABLE 1

| | Organic element analysis | |
|---|---|---|
| | Measured Value (%) | Theoretical Value (%) |
| C | 54.66 | 54.66 |
| H | 4.28 | 4.37 |
| N | 9.26 | 9.11 |
| S | 7.16 | 6.95 |

Results of Infrared Spectroscopy (KBr Pellet Method):

TABLE 2

Infrared absorption peak and attribution (KBr pellet)

| Absorption Peak Position | Absorption Intensity | Possible Group Attribution |
|---|---|---|
| 2419-2833 | w | V CH3, CH2 |
| 1805 | s | V C=O (ester) |
| 1715 | s | V C=O (carboxylic acid) |
| 1628 | s | V C=O (ketone) |
| 1628-1505 | s | V C=C (aromatic ring, heterocycle) |
| 1470 | s | δ CH3, CH2 |
| 1394 | m | δ OH |
| 1234 | s | V C—O |
| 1134 | m | |

Notes:
V: stretching vibration;
δ: Flexural vibration;
s: strong absorption;
m: medium absorption;
w: weak absorption

Results of Mass Spectrometry:
Ms(FAB):m/z462(M+1), 461, 444, 360.

Results of $^1$HNMR Spectrum:
$^1$HNMR spectrum data and attribution analysis were shown in the following table (solvent DMSO-$d_6$):

TABLE 3

Hydrogen spectrum analysis

| Spectral Peak Serial Number | Chemical Shift δ (ppm) | Multiplicity | Proton Number | Coupling Constant J (Hz) | Remark |
|---|---|---|---|---|---|
| a | 2.12 | d | 3 | 6 | H27 |
| b | 2.13 | s | 3 | | H26 |
| c | 2.64 | m | 4 | | H16, H18 |
| d | 3.31 | m | 4 | | H15, H19 |
| e | 3.46 | s | 2 | | H20 |
| f | 6.37 | q | 1 | 6 | H9 |
| g | 6.88 | d | 1 | 7.5 ($^4J_{HF}$) | H10 |
| h | 7.75 | d | 1 | 14 ($^3J_{HF}$) | H13 |
| i | 14.55 | brs | 1 | | OH |

Results of $^{13}$CNMR Spectrum:
$^{13}$CNMR spectra data and attribution analysis of product were shown in the following table (solvent DMSO-$d_6$):

TABLE 4

Carbon spectrum analysis

| Spectral Peak Serial Number | Chemical Shift Δ (ppm) | Multiplicity | Carbon Atom Number | Remark |
|---|---|---|---|---|
| A | 8.57 | q | 1 | C26 |
| B | 20.17 | q | 1 | C27 |
| C | 49.04 | t | 1 | C20 |
| D | 49.19 | t | 2 | C15, C19 |
| E | 51.32 | t | 2 | C16, C18 |
| F | 72.15 | d | 1 | C9 |
| G | 101.53 | s | 1 | C2 |
| H | 102.32 | d | 1 | C10 |
| I | 112.01 | d ($^2J_{CF}$) | 1 | C13 |
| J | 117.18 | d ($^3J_{CF}$) | 1 | C4 |
| K | 134.34 | s | 1 | C25 |
| L | 135.68 | s | 1 | C5 |
| M | 138.30 | s | 1 | C21 |
| N | 144.87 | d ($^2J_{CF}$) | 1 | C11 |
| O | 151.70 | d ($^1J_{CF}$) | 1 | C12 |
| P | 152.26 | s | 1 | C23 |

TABLE 4-continued

Carbon spectrum analysis

| Spectral Peak Serial Number | Chemical Shift Δ (ppm) | Multiplicity | Carbon Atom Number | Remark |
|---|---|---|---|---|
| Q | 163.22 | s | 1 | C7 |
| R | 165.61 | s | 1 | C1 |
| S | 175.49 | d ($^4J_{CF}$) | 1 | C3 |

Conclusion:
Based on the assays hereinbefore, it can be determined that molecular structure of the sample is prulifloxacin, as shown below:

Experimental Example 2

Confirmation of Configuration of Samples

The following assays were conducted on the samples prepared in Examples 1-4.
1. Determination of Specific Rotation
    The result of the assay was shown in Table 5.
2. Determination Contents and Calculation of e.e. Values
    Contents of levo-enantiomer and dextro-enantiomer in the sample were determined by chiral high performance liquid chromatography as described below and e.e. values were calculated.
Method of Chiral High Performance Liquid Chromatography Used for Optical Isomers of Uliflourxacin:
    octadecylsilane chemically bonded silica was used as filler; chiral solution of L-isoleucine (prepared by dissolving 1.04 g of L-isoleucine and 0.50 g of copper sulfate in 1,000 mL of water)-methanol (83:17) was used as mobile phase; flow rate was 1.0 mL per minute; detection wavelength was 330 nm. Appropriate amount of said sample was dissolved in the mobile phase and diluted with the mobile phase to prepare a solution, every 1 mL of which contains 1 mg of said sample. 10 µl of the solution was charged into liquid chromatograph. The theoretical plate number, calculated based on peak of levo-uliflourxacin, was no less than 4,000. Resolution between levo-uliflourxacin and dextro-uliflourxacin should comply with requirements. Contents were determined by normalization.
Method of Chiral High Performance Liquid Chromatography Used for Optical Isomers of Prulifloxacin:
    octadecylsilane chemically bonded silica was used as filler; chiral solution of L-isoleucine (prepared by dissolving 1.04 g of L-isoleucine and 0.50 g of copper sulfate in 1,000 mL of water)-methanol (85:15) was used as mobile phase; flow rate was 1.0 mL per minute; detection wavelength was 330 nm. Appropriate amount of said sample was dissolved in the mobile phase and diluted with the mobile phase to prepare a solution, every 1 mL of which contains 1 mg of said sample. After heating reflux at 80° C. for 1 hour followed by cooling, 10 μl of the solution was charged into liquid chromatograph. The theoretical plate number, calculated based on peak of levo-prulifloxacin, was no less than 4,000. Resolution between levo-prulifloxacin and dextro-prulifloxacin should comply with requirements. Contents were determined by normalization.

Results of the Assay Were Shown in Table 5.

TABLE 5

| Example | Specific Rotation $[\alpha]^{20}_D$ | e.e. Values |
|---|---|---|
| 1 | −133° (c = 0.5, 0.1 mol/L methanesulfonic acid) | 96% |
| 2 | +132.4° (c = 0.5, 0.1 mol/L methanesulfonic acid) | 96% |
| 3 | −108° (c = 0.5, 0.1 mol/L methanesulfonic acid) | 96% |
| 4 | +108° (c = 0.5, 0.1 mol/L methanesulfonic acid) | 96% |

3. Determination of Circular Dichroism of the Samples Prepared in Examples 3-4

Figure 4:
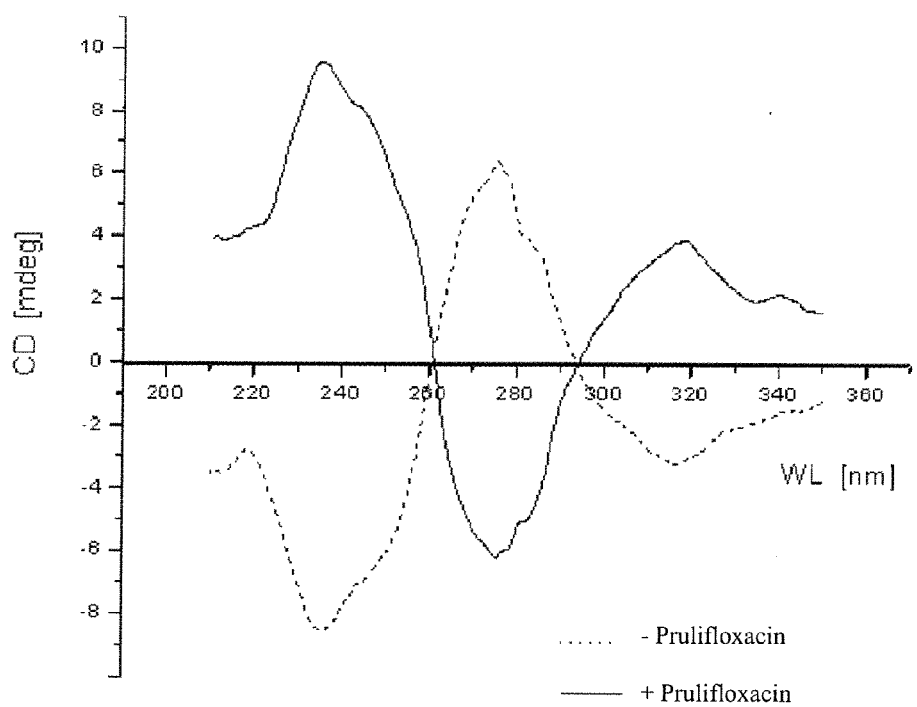
FIG. 4 depicts circular dichroism spectrograms of levo-prulifloxacin and dextro-prulifloxacin (solvent:acetonitrile, C=20 μg/ml), where the dashed curve indicates levo-prulifloxacin and the solid curve indicates dextro-prulifloxacin.

The result of the assay was depicted in FIG. 4

The result of the assay above may prove that: The products retained the same property of polarized light as the raw material (that is levorotatory ulifloxacin produced levorotatory prulifloxacin while dextrorotatory ulifloxacin produced dextrorotatory prulifloxacin). The chiral high performance liquid chromatography suggests that the ratios of two optical isomers before or after reaction remain unchanged, which proves configuration of the chiral center 1-C was maintained the same. Thus, the prulifloxacin prepared from the raw material S-ulifloxacin still keeps the same S configuration and the final product is S-prulifloxacin.

The present invention studied absorption features of S-(−)-prulifloxacin and R-(+)-prulifloxacin on the circular polarized light by circular dichroism spectroscopy. The two spectrograms are mirror images of each other, which proves that S-(−)-prulifloxacin and R-(+)-prulifloxacin are enantiomer of each other.

Comparing the circular dichroism spectrogram as depicted in FIG. 4 with the circular dichroism spectrogram of analogue of the similar structure with known absolute configuration as disclosed in the publication Chem. Pharm. Bull. 47(12) 1765-1773 (1999), it was found that (−)-prulifloxacin has similar Cotton effect with the two analogues reported in the publication, ethyl S-(−)-6,7-difluoro-1-methyl-4-oxo-4H-[1,3]thiazeto[3,2-α]quinoline-3-carboxylate and ethyl S-(−)-6,7-difluoro-1-fluoromethyl-4-oxo-4H-[1,3]thiazeto[3,2-α]quinoline-3-carboxylate; so does (+)-prulifloxacin. The results also verify on the other hand that the absolute configuration of levo-prulifloxacin of the present invention is S type while the absolute configuration of dextro-prulifloxacin is R type.

Conclusion:

The absolute configuration of the sample prepared in Example 3 is S configuration, as shown in the formula below:

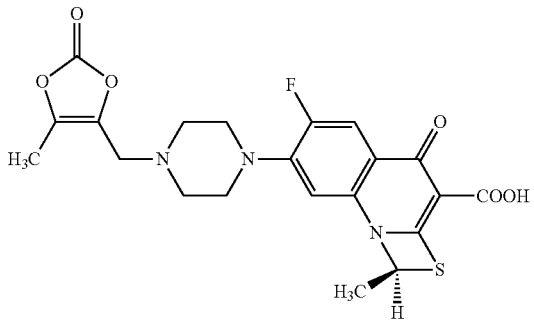

Example 5

Preparation of S-(−)-Prulifloxacin 3.49 g (0.01 mol) of S-(−)-uliflourxacin, 1.2 g (0.012 mol) of anhydrous potassium bicarbonate and 20 ml of dimethylsulfoxide were mixed and stirred. 0.012 mol of DMDO-Br in DMSO (5 mL) solution was added dropwise at −20° C. Stirring proceeded at −20° C. for 3 hours. The reaction solution was poured into 100 ml of ice water, and the pH value was adjusted to 7 with 20% acetic acid. The solution was filtered after stirring for 30 minutes. The filter residue was washed with water. The solid was collected and dried under vacuum. After recrystallization from acetonitrile, 2.5 g of the target product levo-prulifloxacin was obtained with a purity of 98% and a yield rate of 54%.

Specific rotation $[\alpha]^{20}_D$=−108° (c=0.5, 0.1 mol/L methanesulfonic acid)

Example 6

Preparation of S-(−)-Prulifloxacin 3.49 g (0.01 mol) of S-(−)-uliflourxacin, 1.04 g (0.008 mol) of N,N-diisopropylethylamine and 20 mL of N,N-dimethylformamide (DMF) was mixed and stirred, 0.008 mol of DMDO-Br in DMF (5 mL) solution was added thereinto. The solution was heating to 60° C. and reacted for 15 minutes. The reaction solution was poured into 100 ml of ice water, and the pH value was adjusted to 7 with 20% acetic acid. The solution was filtered after stirring for 30 minutes. The filter residue was washed with water. The solid was collected and dried under vacuum. After recrystallization from acetonitrile, 2.0 g of the target product levo-prulifloxacin was obtained with a purity of 98% and a yield rate of 43%.

Specific rotation $[\alpha]^{20}_D$=−108° (c=0.5, 0.1 mol/L methanesulfonic acid)

Example 7

Preparation of S-(−)-Prulifloxacin 10 g (0.029 mol) of S-(−)-uliflourxacin, 30 ml of N,N-dimethylacetylamide and 14.7 g (0.145 mol) of triethylamine was mixed and cooled to 5~10° C. 8.5 g (0.03 mol) 4-(p-toluenesulfonic acid-1-methyl ester)-5-methyl-1,3-dioxolen-2-one in 25 ml of N,N-dimethylacetylamide solution was added dropwise while stirring. After addition, the solution was reacted at room temperature for 10 hours. The reaction solution was poured into 200 ml of ice water, and the pH value was adjusted to 7 with 20% acetic acid. The solution was filtered after stirring for 30 minutes. The filter residue was washed with water. The solid was collected and dried under vacuum. After recrystallization from acetonitrile, 7.46 g of the target product levo-pruliflouxacin was obtained with a purity of 98% and a yield rate of 57%. Specific rotation $[\alpha]^{20}_D = -108°$ (c=0.5, 0.1 mol/L methanesulfonic acid).

Example 8

Preparation of S-(−)-Prulifloxacin 3.49 g (0.01 mol) of S-(−)-uliflourxacin, 0.79 g (0.05 mol) of potassium carbonate and 20 ml of dimethylformamide (DMF) was mixed and stirred. 0.012 mol of DMDO-Br in DMF (5 ml) solution was added at −10° C. At the same temperature, the solution was reacted for 2 hours. The reaction solution was poured into 100 ml of ice water, and the pH value was adjusted to 7 with 20% acetic acid. The solution was filtered after stirring for 30 minutes. The filter residue was washed with water. The solid was collected and dried under vacuum. After recrystallization from acetonitrile, 2.2 g of the target product levo-prulifloxacin was obtained with a purity of 98% and a yield rate of 48%. Specific rotation $[\alpha]^{20}_D = -108°$ (c=0.5, 0.1 mol/L methanesulfonic acid).

Example 9

Preparation of S-(−)-Prulifloxacin 3.49 g (0.01 mol) of S-(−)-uliflourxacin, 0.79 g (0.02 mol) of diisopropylamine and 20 ml of dimethylformamide (DMF) was mixed and stirred. 0.02 mol of DMDO-Br in DMF (5 ml) solution was added at 0° C. At the same temperature, the solution was reacted for 2 hours. The reaction solution was poured into 100 ml of ice water, and the pH value was adjusted to 7 with 20% acetic acid. The solution was filtered after stirring for 30 minutes. The filter residue was washed with water. The solid was collected and dried under vacuum. After recrystallization from acetonitrile, 2.5 g of the target product levo-prulifloxacin was obtained with a purity of 98% and a yield rate of 54%. Specific rotation $[\alpha]^{20}_D = -108°$ (c=0.5, 0.1 mol/L methanesulfonic acid).

Example 10

Preparation of R-(+)-Prulifloxacin

In accordance with the method as described in Example 5, the raw material R-(+)-prulifloxacin was prepared to 2.5 g of the target product R-(+)-prulifloxacin with a purity of 98% and a yield rate of 54%. Specific rotation $[\alpha]^{20}_D = +108°$ (c=0.5, 0.1 mol/L methanesulfonic acid).

Example 11

Preparation of Levo-Prulifloxacin Hydrochloride

S-(−)-6-fluoro-1-methyl-7-[4-(5-methyl-2-oxo-1,3-dioxolen-4-yl)methyl-1-piperazinyl]-4-oxo-4H-[1,3]thiazeto[3,2-α]quinoline-3-carboxylic acid hydrochloride 0.5 g of S-(−)-prulifloxacin was dissolved in 15 mL of chloroform and then 0.5 mL of 33% (v/v) hydrochloric acid-methanol solution was added while stirring. The solution was filtered and the filtration residue was washed with methanol. The collected solid was dried to obtain 450 mg said compound with a yield rate of 83%. The melting point of the product is higher than 220° C. (the sample became darker during the test).

Example 12

Preparation of Levo-Prulifloxacin Mesylate

S-(−)-6-fluoro-1-methyl-7-[4-(5-methyl-2-oxo-1,3-dioxolen-4-yl)methyl-1-piperazinyl]-4-oxo-4H-[1,3]thiazeto[3,2-α]quinoline-3-carboxylic acid mesylate 0.5 g of S-(−)-prulifloxacin was dissolved in 15 mL of chloroform and then 0.5 mL of 50% methanesulfonic acid-methanol solution was added while stirring. The solution was filtered and the filtration residue was washed with methanol. The collected yellow solid was dried with calcium chloride under vacuum for 24 hours and further dried with calcium chloride at 80° C. under vacuum for 5 hours to obtain 470 mg said compound with a yield rate of 78%. The melting point of the product is higher than 220° C. (the sample became darker during the test).

Example 13

Preparation of Levo-Prulifloxacin Hydrochloride 0.5 g of S-(−)-prulifloxacin was dissolved in 15 mL of chloroform and then 0.5 mL of 33% (v/v) hydrochloric acid-methanol solution was added while stirring. The solution was dried by evaporation. Methanol was added to the residue and stirred for 10 minutes. The solution was filtered and the filtration residue was washed with methanol. The collected solid was dried to obtain 460 mg said compound with a yield rate of 85%.

Example 14

Preparation of Film-Coated Tablet of Levo-Prulifloxacin

Prescription Composition of Core Tablet

| Raw and adjuvant materials | Amount |
| --- | --- |
| Levo-prulifloxacin | 132.1 g |
| Lactose | 25 g |
| Microcrystalline cellulose | 10 g |
| Starch | 5 g |
| Hydroxypropyl cellulose | 6 g |
| Croscarmellose sodium | 4 g |
| Gas phase silicon | 0.4 g |
| Magnesium stearate | 1 g |
| 3% Hydroxypropyl methylcellulose in 75% ethanol | 85~90 g |

1,000 tablets were prepared in total. Each tablet weighing around 200 mg contains 132.1 mg of levo-prulifloxacin.

Prescription Composition of Coating Solution

Amount needed for 1 kg of core tablet:

| Opadry (OY-C-7000A), white | 35 g |
|---|---|
| 95% ethanol | 402.5 g |

Preparation of Core Tablet:

Raw and adjuvant materials were sieved through 80-mesh sieves and prescription amount of each kind of material was weighted and mixed evenly. Appropriate amount of 3% hydroxypropyl methylcellulose in 75% ethanol solution was then added to prepare soft material which was granulated with 16-mesh sieve and dried at 55° C.±5° C. and finished granule with 16-mesh sieve. Hydroxypropyl cellulose, croscarmellose sodium, gas phase silicon and magnesium stearate were added and mixed evenly. After determining the content, granules were pressed by shallowly arc-shaped punches of Φ8.5 mm to prepare tablets, weight of which is 200 mg/tablet and hardness of which is 8-11 kg.

Preparation of Coating Solution (for 1 Kg of Core Tablets):

402.5 g of 95% ethanol was added into a container placing on a stirrer. After turning on the stirrer, 35 g of white powder of Opadry (OY-C-7000A) was added while stirring and then mixed evenly. Coating was conducted while stirring as well.

Core tablets were charged into coating pot, which was then preheated at 60° C.±5° C. Coating machine was switched on, followed by adjusting rotation speed. When pot temperature reached around 45° C., peristaltic pump was started to spray the coating solution onto the surface of core tablets while conducting appearance inspection until the coating solution ran out.

Example 15

Preparation of Film-Coated Tablet of Levo-Prulifloxacin Hydrochloride

Prescription Composition of Core Tablet:

| Raw and adjuvant materials | Amount |
|---|---|
| Levo-prulifloxacin hydrochloride | 142.5 g |
| Lactose | 25 g |
| Microcrystalline cellulose | 10 g |
| Starch | 5 g |
| Hydroxypropyl cellulose | 6 g |
| Croscarmellose sodium | 4 g |
| Gas phase silicon | 0.4 g |
| Magnesium stearate | 1 g |
| 3% Hydroxypropyl methylcellulose in 75% ethanol | 85~90 g |

1,000 tablets were prepared in total. Each tablet weighing around 200 mg contains 132.1 mg of the effective component levo-prulifloxacin.

Film-coated tablets of levo-prulifloxacin hydrochloride were prepared by the method as described in Example 14.

Therapeutic effects of said compound of the present invention were proved by the following experimental examples.

Experimental Example 3

Experiment on Systemic Infection in Mouse

Testing Method
1. Origin of testing samples:
Levo-ofloxacin was commercially available.
Prulifloxacin was self-made product, prepared according to the method disclosed in the publication J. Med. Chem. 1992, 35, 4727-4738.
Levo-prulifloxacin, dextro-prulifloxacin, levo-prulifloxacin hydrochloride, levo-prulifloxacin mesylate were self-made, prepared according to the method described in examples (see respective ordinal number in parenthesis following name of testing drug in Table 6);
2. Experimental strains: Bacteria for infecting animals were pathogenic strains isolated from clinic;
3. Preparation of liquid bacteria culture: 2-3 colonies were picked and inoculated into M-H broth, followed by incubation for 18 hours at 37° C. The culture was diluted appropriately with 5% dried yeast liquid for use.
4. Experimental animals: Healthy SPF Kunming mice were selected, with 18-22 g in body weight, half male and half female.
5. Determination of minimal lethal dose of bacteria: Mice were divided randomly, resulting in 10 mice in each group, half male and half female. The above-mentioned bacterial cultures in different dilutions were injected intraperitoneally into mice, in the amount of 0.5 mL per mouse, followed by continuous observation for 7 days after infection and recording the number of death mice. The minimal amount of bacteria which caused 100% death of mice was deemed as minimal lethal dose of bacteria and thereby was adopted for infection tests in vivo.
6. Preparation of testing drugs: The testing drugs were prepared with 1% CMC, respectively.
7. Method for infection and treatment: Experimental animals were divided randomly but evenly based on gender and body weight, resulting in 10 mice in each group, half male and half female. Minimal lethal dose of bacteria were injected intraperitoneally into mice in amount of 0.5 mL/mice, respectively. After infected for 1 hour, the testing drugs in different doses were administered to mice by gavage in the amount of 0.2 ml/10 g, respectively. Seven dose groups of 0.05, 0.10, 0.20, 0.40, 0.80, 1.60, 3.20 mg/kg were set up for *Escherichia coli* while seven dose groups of 0.50, 1.0, 2.0, 4.0, 8.0, 16.0, 32.0 mg/kg were set up for *Pseudomonas aeruginosa*. Observation was conducted after administration and death statuses of the mice were recorded. A control group was set up and the number of mice which died within 7 days after infection was recorded at the same time. The obtained data were processed by Bliss method to calculate $ED_{50}$.
8. The results were listed in Table 6.

TABLE 6

Therapeutic effects of said compounds of the present invention on systemic infection in mouse infection models

| | $ED_{50}$ mg/kg | |
|---|---|---|
| Testing Drugs | E. coli | P. aeruginosa |
| Ofloxacin (commercially available) | 0.82 | 16.08 |
| (+/−) Prulifloxacin (Self-made) | 0.53 | 4.04 |
| (−) Prulifloxacin (Sample prepared in Example 3) | 0.11 | 1.02 |
| (+) Prulifloxacin (Sample prepared in Example 4) | 1.58 | 8.20 |

TABLE 6-continued

Therapeutic effects of said compounds of the present invention on systemic infection in mouse infection models

| Testing Drugs | $ED_{50}$ mg/kg | |
|---|---|---|
| | E. coli | P. aeruginosa |
| (−) Prulifloxacin hydrochloride (Sample prepared in Example 11) | 0.12 | 1.25 |
| (−) Prulifloxacin mesylate (Sample prepared in Example 12) | 0.11 | 1.22 |

Conclusion:

Said compounds of the present invention have very strong therapeutic effects on infection in mice. In comparison with racemate, therapeutic effects of levo-prulifloxacin are increased remarkably. Salts of levo-prulifloxacin have similar effects with levo-prulifloxacin.

Experimental Example 4

Acute Toxicity Test on Levo-Prulifloxacin

Method:

Acute toxicity test was conducted in NIH mice by administrating limited-dosages of drugs.

Testing Group:

Levo-prulifloxacin; control groups: racemic prulifloxacin group and blank control group 20 NIH mice in each group, half male and half female, 18~22 g in body weight, were fasted overnight. Levo-prulifloxacin and racemic prulifloxacin were prepared to a 250 mg/ml suspension with 0.3% CMC, respectively, and then administered to the mice by gavage at once in the amount of 0.2 mL/10 g. After administration, observation was firstly conducted for 4 hours continuously, and then once a day for 2 weeks continuously. Animals' responses to toxicity, appearing time and recovering time thereof were recorded. On Day 2, 4, 8, 11 and 15, body weight of the animals were measured and amounts of feed intake were determined. Observation indexes included diet, appearance, behavior, secretion, excrement and the like Animals' death was recorded, starting time, severity, duration of toxic symptoms and toxic reactions, whether the symptoms or reactions are reversible and the like were also recorded. Animals dying from poisoning and dying animals were dissected roughly in time while all other animals were dissected roughly after completing observation. When changes in such as volume, color, texture and etc. were observed in any organs, histopathological examination was conducted on the changed organs. The obtained data were processed by Bliss method to calculate $LD_{50}$.

Results:

No abnormalities were observed in animals in each group after administration. No animal death occurred. Body weight of all the animals was increased normally and no significant differences were observed among the groups. Pathological anatomy results showed no abnormalities in organs or tissues, which suggested that the compound of the present invention has very low toxicity and $LD_{50}$ of oral administration of levo-prulifloxacin and racemic prulifloxacin in mice are all higher than 5,000 mg/kg.

Accordingly, the compound of the present invention may be used for treating systemic infection and local infections including respiratory tract infection, urinary tract infection and biliary tract infection, and can be safe for use in mammals including humans.

The invention claimed is:

1. An optically active compound of prulifloxacin as shown in the general formula 1 below or physiologically acceptable pharmaceutical salts thereof, wherein their stereo configurations are S configuration and they have optical activity of levorotatory polarized light:

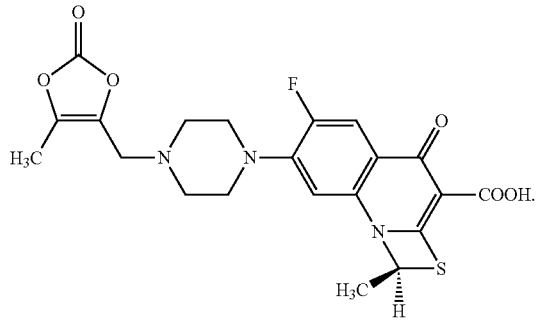

(I)

2. An anti-infection pharmaceutical composition, comprising oral preparation containing optically active compound of prulifloxacin or physiologically acceptable pharmaceutical salts thereof according to claim 1 as effective components and pharmaceutical adjuvants.

3. A preparation method of optically active compound of prulifloxacin according to claim 1, wherein the method comprises:

utilizing levo-ulifloxacin shown in formula 2 below and the compound shown in formula 3 below as raw materials; and reacting the raw materials in an organic solvent in the presence of an alkaline material at a reaction temperature and a reaction time,

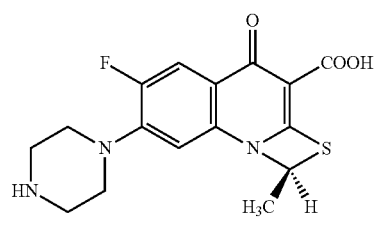

2

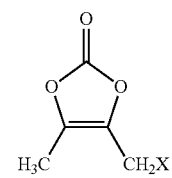

3 wherein X in formula 3 is a halogen or p-methylsulfonyloxy group;

the reaction temperature is −20~60° C. and the reaction time is 15 minutes to 24 hours;

the ratio of levo-ulifloxacin to the compound of formula 3 to said alkaline material is 1:0.8~2:0.5~5 by gram molecule; and said alkaline material is inorganic base or organic base.

4. The preparation method of optically active compound of prulifloxacin according to claim 3, wherein the inorganic base is potassium carbonate, potassium bicarbonate, sodium carbonate, sodium bicarbonate, calcium carbonate or calcium bicarbonate; and the organic base is triethylamine, diisopropylamine, N,N-Diisopropylethylamine, tributylamine, N-methylmorpholine, N,N-dimethylaniline or imidazole.

5. The preparation method of optically active compound of prulifloxacin according to claim 4, wherein the inorganic base is potassium carbonate, potassium bicarbonate, triethylamine, diisopropylamine, or N,N-diisopropylethylamine.

6. The preparation method of optically active compound of prulifloxacin according to claim 3, wherein the X in formula 3 is bromine, which means the chemical name of said compound is 4-bromomethyl-5-methyl-1,3-dioxolen-2-one.

7. The preparation method of optically active compound of prulifloxacin according to claim 3, wherein the reaction temperature is −10~30° C. and the reaction time is 15 minutes to 24 hours.

8. The preparation method of optically active compound of prulifloxacin according to claim 3, wherein the organic solvent is N,N-dimethylformamide or N,N-dimethylacetylamide or dimethyl sulfoxide.

9. A method of treating infection, the method comprising:
using the optically active compound of prulifloxacin according to claim 1 as anti-infection drugs.

* * * * *

UNITED STATES PATENT AND TRADEMARK OFFICE
CERTIFICATE OF CORRECTION

| | |
|---|---|
| PATENT NO. | : 8,501,741 B2 |
| APPLICATION NO. | : 13/522290 |
| DATED | : August 6, 2013 |
| INVENTOR(S) | : Jun Ying et al. |

It is certified that error appears in the above-identified patent and that said Letters Patent is hereby corrected as shown below:

On the Title Page

(86) § 371 (c)(1), (2), (4) Date      Delete "Jul. 13, 2002"

Insert --Jul. 13, 2012 --

In the Specification

Column 1, line 26      Delete "drugs"

Insert -- drug --

Column 1, line 60      Delete "effects"

Insert -- effect --

Column 8, line 56      Delete "Analsis"

Insert -- Analysis --

Column 17, line 40      Delete "were"

Insert -- was --

Signed and Sealed this
Twenty-first Day of April, 2015

Michelle K. Lee
*Director of the United States Patent and Trademark Office*